United States Patent [19]

Penrose

[11] Patent Number: 5,720,714
[45] Date of Patent: Feb. 24, 1998

[54] PADDING

[75] Inventor: Jane Edith Penrose, Skipton, United Kingdom

[73] Assignee: Smith & Nephew plc., London, United Kingdom

[21] Appl. No.: 635,901

[22] PCT Filed: Nov. 3, 1994

[86] PCT No.: PCT/GB94/02410
§ 371 Date: May 3, 1996
§ 102(e) Date: May 3, 1996

[87] PCT Pub. No.: WO95/12373
PCT Pub. Date: May 11, 1995

[30] Foreign Application Priority Data

| Nov. 3, 1993 | [GB] | United Kingdom | 9322658 |
| Nov. 4, 1993 | [GB] | United Kingdom | 9322716 |
| Nov. 4, 1993 | [GB] | United Kingdom | 9322719 |
| Apr. 6, 1994 | [GB] | United Kingdom | 9406777 |

[51] Int. Cl.$^6$ ............................................. A61F 5/00
[52] U.S. Cl. .................... 602/6; 602/3; 602/42; 602/46; 602/52; 128/888
[58] Field of Search ............... 602/3, 5, 6, 9, 602/8, 42, 46, 52; 428/71, 159, 315.9, 343, 422; 128/888, 889

[56] References Cited

U.S. PATENT DOCUMENTS

| 4,516,572 | 5/1985 | Schlein | 602/3 |
| 5,364,339 | 11/1994 | Carver | 128/888 X |
| 5,445,604 | 8/1995 | Lang | 602/47 |

FOREIGN PATENT DOCUMENTS

| 397999 | 11/1990 | European Pat. Off. | 428/71 |
| 8607533 | 12/1986 | WIPO | 602/8 |
| WO95/03018 | 2/1995 | WIPO . | |

*Primary Examiner*—Richard J. Apley
*Assistant Examiner*—Kim M. Lee
*Attorney, Agent, or Firm*—Larson & Taylor

[57] ABSTRACT

There are described padding materials comprising a first moisture vapor permeable film layer and a second moisture vapor permeable film layer with air bubbles spaced therebetween. The air bubbles may optionally contain foam pips. Methods of preparation and uses of the padding materials are also described.

13 Claims, 3 Drawing Sheets

PADDING

BACKGROUND OF THE INVENTION

This invention relates to novel forms of padding for use under rigid casts used in the repair of, eg. bone fractures, or for use as a pressure relieving dressing and methods for their manufacture.

Padding materials for placing beneath an orthopaedic cast usually comprise soft conformable materials such as natural or synthetic non-woven materials, eg. those sold by Smith & Nephew Medical in the UK under the name SOFFBAN.

However, such materials suffer from the disadvantage that they are generally unsuitable for use with water hardenable resin orthopaedic casts. Moreover, once such resin casts are set they can be brought into contact with water without any deterioration occurring, thus giving the patient much more freedom to carry on a normal life. However, since the underpadding absorbs water and generally suffers damage to its structure when in contact with water this limits the patient's freedom. Also, the use of conventional waterproof materials if left in place for long periods of time may cause the skin to macerate.

Although pressure relieving dressings do not require to be waterproof, such dressings may still cause maceration of the skin if left in place for long periods of time. Hereinafter, orthopaedic undercast padding materials and pressure relieving dressings will be referred to jointly as padding materials.

Breathable foam filled padding materials are known from U.S. Pat. No. 5,102,711 which describes an underpadding comprising a middle layer of foam and top and bottom outer protective layers of polytetrafluoroethylene (PTFE) impregnated with a hydrophilic polyurethane layer. A "quilt bond" is formed by heat sealing the materials together such that the outer PTFE layers only contact at the peripheral bond seams.

However, such materials suffer from a number of disadvantages in that they are expensive to manufacture, lack sufficient conformability and under extremes of pressure the foam padding layer may collapse.

SUMMARY OF THE INVENTION

We have now surprisingly found a form of padding material which overcomes or mitigates these disadvantages.

According to the invention we provide a padding material comprising a first moisture vapour permeable film layer and a second moisture vapour permeable film layer wherein a plurality of air bubbles are spaced between the first and second film layers.

DESCRIPTION OF PREFERRED EMBODIMENTS

The air bubbles spaced between the first and second film layers may protrude from one layer or alternatively, the air bubbles may protrude from both layers.

The moisture vapour permeable films may be adhered together by applying a layer of adhesive to one or both of the first and second film layers. Alternatively, the two films may be heat sealed together.

The air bubbles may be any conventional shape, eg. square, round, pentagonal, hexagonal, etc. Preferred bubble shapes are those which are less prone to being capable of being knocked Whilst the dressing is in use. If the air bubbles are such a shape such that they possess corners, eg. square, then the corners are preferably rounded.

The air bubbles may be from 0.5 to 2.0 cm in diameter, preferably 1 cm in diameter. The thickness of the air bubbles may be from 1 to 10 mm, preferably 3 to 6 mm and most preferably 4 to 5 mm. The air bubbles are preferably spaced such that there is a free area where no air is present. Thus the air bubbles may be spaced a distance of twice their diameter (measured from the centre of the air bubble) from its nearest neighbour. For example an air bubble of 1 cm diameter would have a centre 2 cm distant from the centre of its nearest neighbour.

In addition to the film layers being adhered together, one or both of the film layers of the padding materials of the invention may be coated with an adhesive layer, for example a pressure sensitive adhesive layer, coated on the non-film surface layer of a film layer. Both the film layer and the adhesive layer are preferably transparent or translucent. The adhesive may be coated over one entire surface of the film layer or over part of it, eg. around the periphery. Alternatively, the dressings may be non-adhesive ones.

Preferably the moisture vapour permeable film employed in the padding material comprises a thin flexible film backing layer to render the material highly conformable.

A suitable moisture vapour permeable film layer used in the padding material of the invention can be any of the thin conformable moisture vapour permeable film layers used on conventional adhesive wound dressings. Preferred materials forming the padding materials of the invention are elastomeric.

Suitably the moisture vapour permeable film layer may comprise any of those materials which are conventionally employed to form thin surgical dressings. Suitable materials include those described in United Kingdom Patent No. 1280631, European Patent Nos. 51935, 91800 and 178740.

Favoured moisture vapour permeable films include those formed from polyether polyurethane, polyester polyurethane, hydrophilic polyurethane and polyester-polyether copolymers.

Suitable polyether polyurethanes are described in U.S. Pat. No. 2,899,411. Suitable polyester polyurethanes are described in U.S. Pat. No. 2,871,218. Apt polyester and polyether polyurethanes are known ESTANE (Trade Mark) available from B F Goodrich and in particular grades 5701, 5702, 5703, 5714F and 580201.

Other favoured materials include hydrophilic polymers such as hydrophilic polyurethanes including those described in United Kingdom Patent No. 2093190B, especially the polyurethane described in Example 2 therein.

Other apt materials are elastomeric polyether polyesters, for example those known as HYTREL (Trade Mark) and polyester polyamides, for example those known as PEBAX (Trade Mark).

An apt polyester-polyether copolymer is known as HYTREL 4056 available from Du Pont.

The thickness of the moisture vapour permeable film backing layer can be from 9 to 100 µM and can suitably be 9 to 80 µm. More suitably the backing layer is 15 to 50 µm thick and can preferably be 20 to 40 µm for example 27.5, 30 µm, 35 µm.

In order to provide a superior padding effect foam may be placed inside the air bubbles. Thus according to the invention we provide a padding material comprising a first moisture vapour permeable film layer and a second moisture vapour permeable film layer and a plurality of foam pips sandwiched between the first and second film layers.

The foam pips may comprise a plurality of foam particles trapped in each air bubble. However, it is preferred that each air bubble comprises an individual foam island.

In the padding materials according to the invention the moisture vapour permeable films are preferably water impermeable. However, when a non-waterproof padding material is required, for example for use as a pressure relieving dressing, and when foam pips are present, at least one of the thin film layers need not be continuous.

Thus, according to the invention we provide a padding material comprising a water impermeable moisture vapour permeable film layer, a water permeable and vapour permeable film layer and a plurality of foam pips sandwiched between the film layers.

The water impermeable and water permeable film layers may optionally comprise an intermediate adhesive layer. The adhesive layer may be coated over one or both film facing surfaces of the foam pips.

The water impermeable layer may comprise an apertured film. A preferred apertured film is in the form of a net. The apertured film or net employed in the padding material of the invention can have an open area which is suitably at least 25%, favourably at least 30% and preferably at least 35% of the area of the film. Similarly, the apertured film can have an open area which is suitably not greater than 90%, favourably not greater than 70% and preferably not greater than 60% of the area of the film.

The apertures in the apertured film or net of the padding material of the invention can suitably be at least 0.7 mm in size and can preferably be at least 0.8 mm in size. Similarly, the apertures can suitably be not greater than 2 mm in size and can preferably be not greater than 1.5 mm in size. The apertures may have a symmetrical shape such as a square, rectangular, circular, oval, diamond or triangular shape or an unsymmetrical shape.

The apertures may be formed by any suitable conventional perforating process. Such processes include mechanical perforation using needles or punches, hot melt perforation of selected areas using for example heated protuberances such as heated needles or embossed rollers or hot fluid such as flame or hot gases and stretching a film or sheet embossed with thinner areas.

Preferred nets for use in the invention are in the form of flexible polymer nets. A polymer net is used herein as a polymer sheet having apertures defined by integral strands and junctures. Such nets may be formed by stretching films or sheets embossed with thinner areas.

Favoured polymer nets comprise an elastomeric polymer and in particular a thermoplastic elastomeric polymer/Such nets of elastomeric polymer can impart "softness" to the surface of the orthopaedic padding material of the invention.

Suitable thermoplastic elastomeric polymers include polyether ester and polyether-polyamide block copolymers, polyurethanes, styrene-butadiene and styrene-isoprene block copolymers, polyisobutadiene and ethylene-vinyl acetate copolymers.

Nets for use in the invention may comprise a blend of elastomeric polymer such as ethylene vinyl acetate copolymer with a compatible polymer or an incompatible polymer such as polyolefine, for example low density polyethylene or polystyrene.

It is a significant difference between the present invention and the prior art of U.S. Pat. No. 5,102,711 that, inter alia, the film and net layer come into contact with one another such that the foam layer is not continuous, thus rendering the material more breathable and more conformable.

Any conventional foam may be used to form the foam pips in the padding material according to the invention. The foam need not be a foam which possesses exudate absorbing properties although such foams are included within the scope of the invention. However, non-absorbent foams are preferred.

When the foam pips comprise islands of foam, the islands may be any conventional shape, eg. square, round, pentagonal, hexagonal, diamond, etc. It is a particularly advantageous feature of the present invention to provide foam islands, which, when the padding material is wrapped around a limb, will interlock with one another. This provides the padding material with the desired conformability whilst still providing an appropriate padding effect and providing lower bulk.

Thus according to the invention we provide a padding material as hereinbefore described wherein the foam islands are adapted to substantially interlock with adjacent foam islands when the undercast padding is wrapped around a patient's limb.

The dimensions of the foam islands may be varied, but the preferred dimensions are from 0.5 to 2.0 cm in width, preferably 1 cm in width, the width shall not be limited to these values. The thickness of the foam islands may be from 1 to 10 mm, preferably 3 to 6 mm and most preferably 4 to 5 mm. The foam islands are preferably spaced such that there is a free area where no foam is present. Thus the foam islands may be spaced a distance of twice their width from its nearest neighbour. For example a foam island of 1 cm width would have a centre 2 cm distant from the centre of its nearest neighbour.

The adhesive used either as an intermediate layer between the film layers or as a coating on the non-film facing surface in the padding material of the invention,may be any of the pressure sensitive adhesives used for coating conventional wound dressings.

Aptly the pressure sensitive adhesive layer may be formed from an adhesive which is conventionally used for contact with the skin. Suitable adhesives are described in United Kingdom Patent No. 1280631 and European Patent Nos. 35399 and 51935. Preferably the adhesive is a polyvinyl ethyl ether adhesive or an acrylate ester copolymer adhesive formed by the copolymerisation of 2-ethylhexyl acrylate, butyl acrylate and acrylic acid.

Favoured adhesives of this type are polyvinyl ether adhesives and acrylic adhesives. An apt acrylic adhesive comprising a copolymer of 47 parts by weight of butyl acrylate, 47 parts by weight of 2-ethylhexylacrylate and 6 parts by weight of acrylic is disclosed in United Kingdom Patent No. 2070631.

The adhesive can be coated as a continuous or discontinuous layer. The layer may be a porous microporous or non-porous breathable layer. Such adhesive coatings will generally have a coating weight per unit areas of 10 to 75 $g/m^2$, more usually of 15 to 65 $g/m^2$ and will preferably have a weight per unit areas of 20 to 40 $g/m^2$. In terms of thickness the adhesive layer may be from 15 to 65 μm thick, preferably from 20 to 40 μm thick.

Padding materials according to the invention may be prepared by casting a solution of the polymer which is to form the water impermeable moisture vapour permeable film layer to form a thin film, coating the film with an adhesive, laying a plurality of foam islands onto the film and then laminating a second film layer or net onto the adhesive layer.

According to the invention we provide a method of manufacturing a padding material as hereinbefore described which comprises;

(i) casting a moisture vapour permeable film onto a support layer;

(ii) coating the moisture vapour permeable film with an adhesive;

(iii) laying a plurality of foam pips onto the adhesive layer;

(iv) laying second film onto the adhesive layer; and (v) laminating the first film and the second film together.

Padding materials comprising air bubbles without foam pips may be manufactured by;

(i) casting a first moisture vapour permeable film onto a support layer, which support layer may optionally be adhesive coated;

(ii) casting a second moisture vapour permeable film onto a multiapertured carrier layer which carrier layer has heat or vacuum applied to it; and (iii) laminating the first and second moisture vapour permeable films together.

The padding material may be placed in a bacteria-proof pack, sealed and sterilised by conventional methods including using ethylene oxide or gamma-irradiation.

Suitably the water impermeable moisture vapour permeable film has a moisture vapour transmission rate, of at least 500 g/m2/24 h at 37° C. and 100% relative humidity difference, more suitably at least 1200 g/m2/24 h and preferably at least 1600 g/m2/24 h, eg. up to 9000 g/m2/24 h and most preferably from 2000 to 3000 g/m2/24h. However, the moisture vapour transmission rate of the apertured film may be considerably higher than the aforementioned values.

The moisture vapour transmission rate of an orthopaedic padding material can be readily determined by the Payne Cup method (in the upright position) described in European Patent No. 46071.

According to the invention we provide a method of treatment of a fracture of a body portion which comprises applying a layer of the undercast padding material according to the invention followed by applying a hardenable casting material.

The method is particularly advantageous in that where the casting material is a water hardenable material, eg. a resin, a body portion dressed in the padding material and a hardenable casting material may be immersed in water. Thus we provide a method of treatment as hereinbefore described wherein the body portion is immersed in water.

According to a further feature of the invention we provide a kit comprising a padding material as hereinbefore described and an orthopaedic casting tape, eg. a resin coated casting tape such as a water hardenable resin coated casting tape.

The invention will now be described, but in no way limited by reference to the accompanying drawings in which FIG. 1 is a cross-section of a padding material wherein air bubbles are formed from depressions in one layer of a moisture vapour permeable film;

Figure 1:
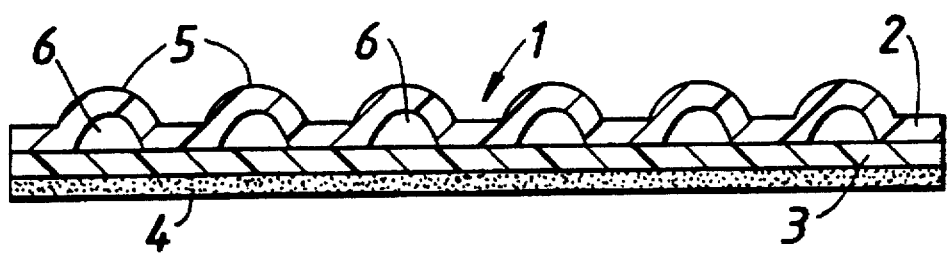

With reference to FIG. 1, a padding material (1) comprises a first moisture vapour permeable film layer (2), a second moisture vapour permeable film layer (3) and an adhesive layer (4). The first film layer (2) comprises a plurality of depressions (5) which encompass air bubbles (6).

Figure 2:
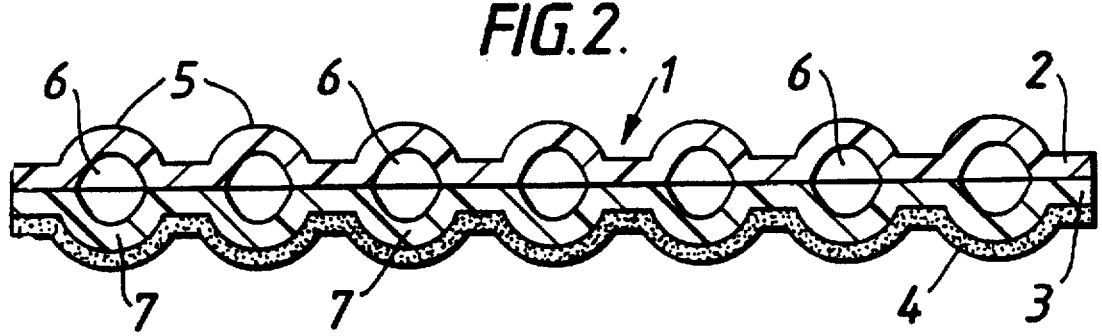
FIG. 2 is a cross-section of a padding material wherein air bubbles are formed from depressions in both layer of moisture vapour permeable film.

Referring to FIG. 2, the first and second moisture vapour permeable film layers (2) and (3) comprises corresponding depressions (5 and 7) which encompasses air bubbles (6).

Figure 3:
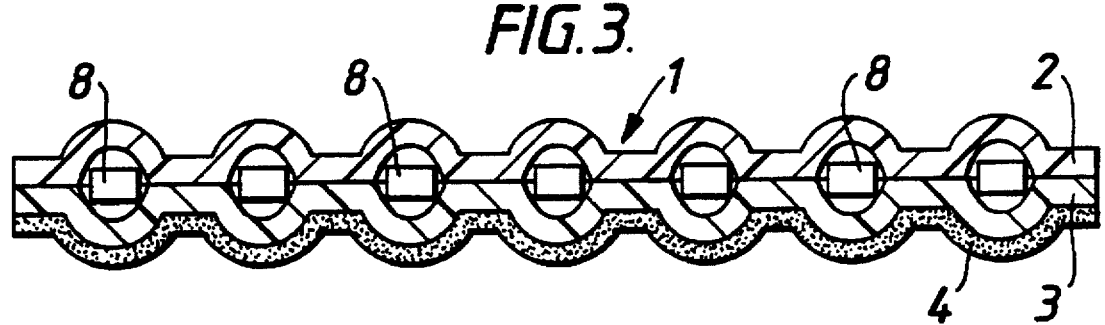
FIG. 3 is a cross-section of a padding material wherein foam chips are sandwiched between two layers of moisture vapour permeable film.

With reference to FIG. 3, a padding material (1) comprises a first moisture vapour permeable film layer (2), a second moisture vapour permeable film layer (3) and an adhesive layer (4). Sandwiched between the film layers (2 and 3) are foam islands (8).

Figure 4:
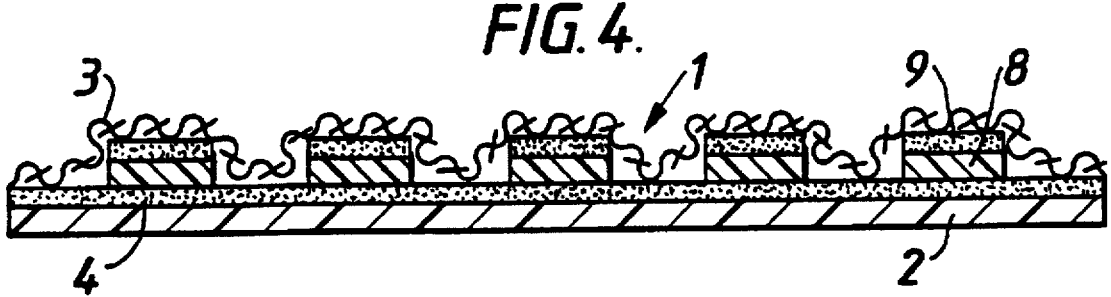
FIG. 4 is a cross-section of a padding material wherein foam islands are sandwiched between two layers of moisture vapour permeable film.

With reference to FIG. 4, a padding material (1) comprises a first moisture vapour permeable film layer (2), a second, moisture vapour permeable film layer (3), eg. a net and an adhesive layer (4). Sandwiched between the film layers (2 and 3) are foam islands (8) which islands are optionally coated with a layer of adhesive (9).

Figure 5:
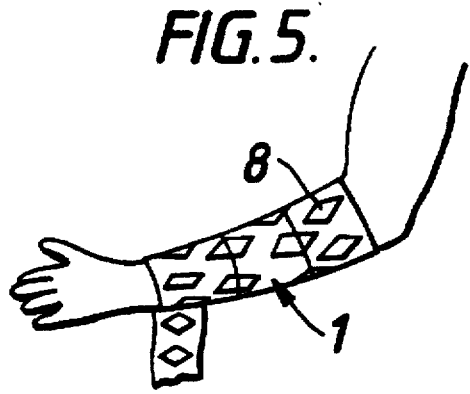
FIG. 5 is a schematic representation of a patient's limb with the padding material of the invention.
Figure 6:
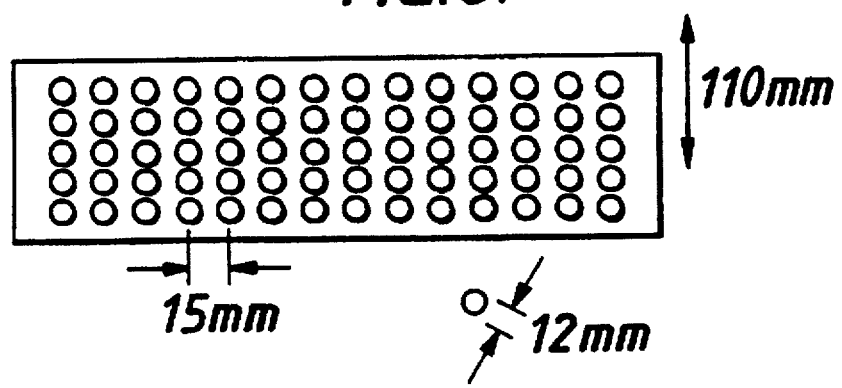
FIGS. 6 to 10 are schematic representations of dressings illustrating alternative foam island shapes.
Figure 7:
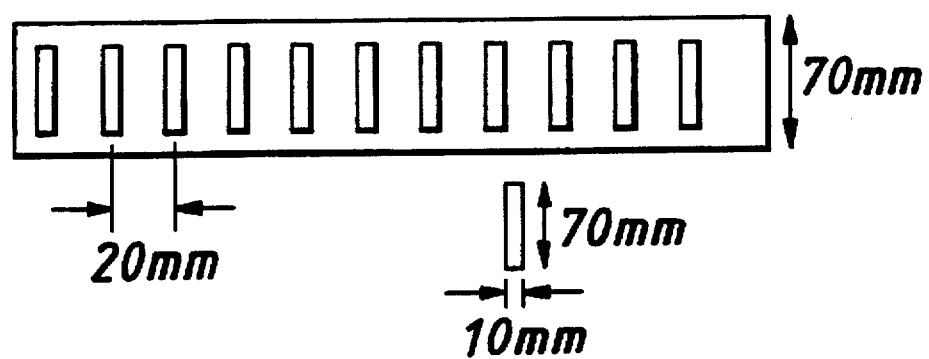
Figure 8:
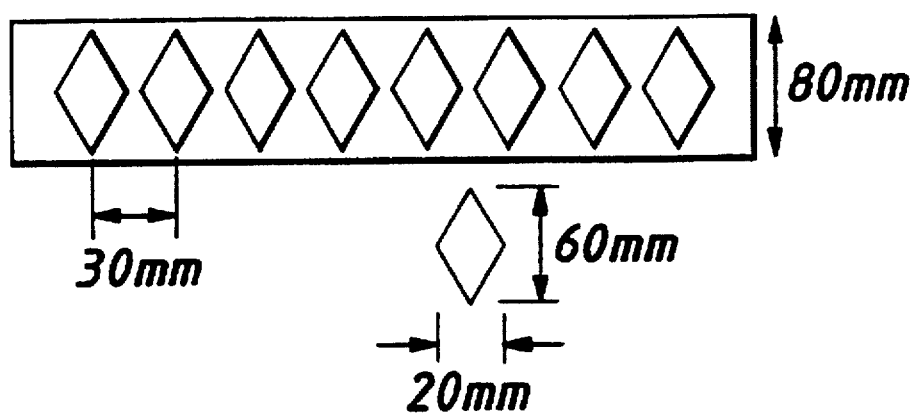
Figure 9:
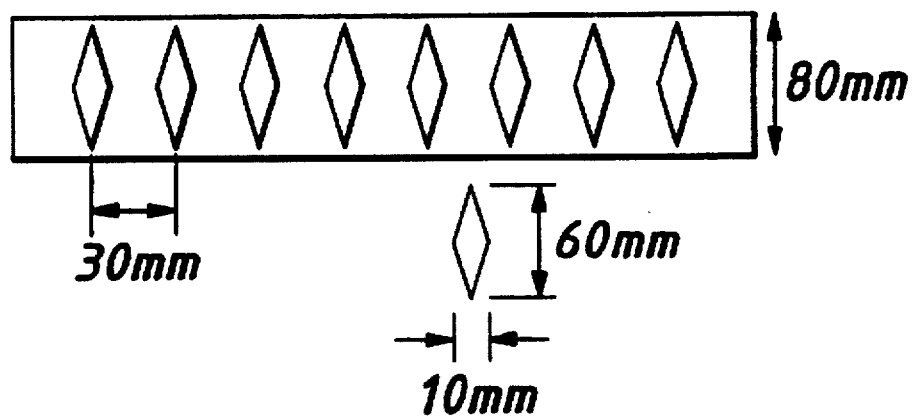
Figure 10:
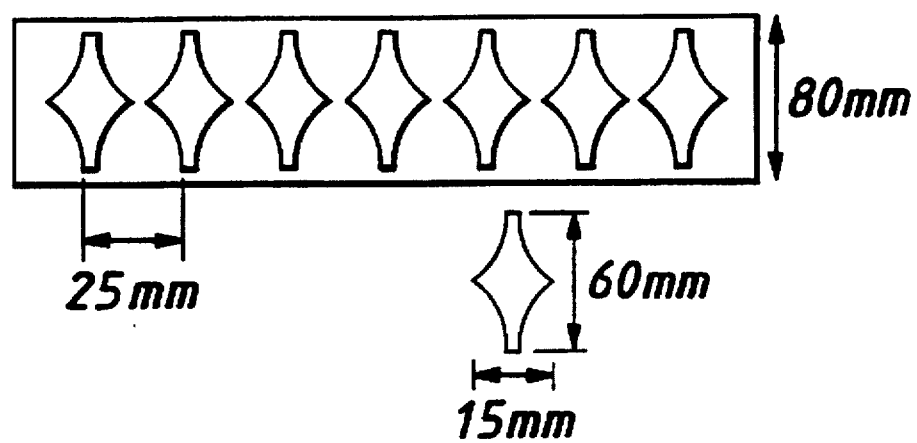

With reference to FIG. 5, in use as a padding, the material (1) is wrapped around a patient's limb such that the foam islands interlock with one another to produce a padding effect.

The invention will now be illustrated but in no way limited by the following Examples.

EXAMPLE 1

Manufacture of an Undercast Padding

An undercast padding was manufactured as a composite of a) polyurethane film
b) adhesive
c) padding
d) net 1. The polyurethane film was manufactured by casting a polyurethane solution (estane/tetrahydrofuran) on to a release coated paper, using well known knife/roller techniques, drying and batching in bulk roll format. The film was controlled to 20–30 $gm^{-2}$.

2. A solvent based acrylic pressure sensitive adhesive was coated onto a release coated paper, at a weight of 20 $gm^{-2}$ using knife/roller technique. After drying, this was laminated to the polyurethane film removing the paper from the film leaving a laminate of polyurethane film/adhesive/release paper. The bulk roll was slit to the appropriate width on a "rewind crush cut slitter".

3. The foam was a 3 mm thick polyethylene foam supplied by Alveo. The shapes were cut to the required dimensions using a die and press.

4. The net used was a 27 $gm^{-2}$ polyethylene net, referenced 12×27 supplied by Smith & Nephew Extruded Films, slit to 80 mm width.

The samples were made by a) Laying the polyurethane/adhesive/paper laminate (2.7 m×80 mm) on a clean surface with the paper uppermost, delaminate the paper leaving the adhesive exposed.

b) Place the shaped foam pads, 25 mm apart.

c) Lay on the Polyethylene net over the pad and adhesive. Ensure intimate contact between adhesive and net by using a roller. Roll up the composite.

A total of 6 padding variants were produced, see FIGS. 6–10.

I claim:

1. A padding material comprising a first moisture vapour permeable film layer and a second moisture vapour permeable film layer wherein a plurality of discrete empty air bubbles are spaced between the first and second film layers.

2. A padding according to clam 1 wherein the air bubbles are from 0.5 to 2.0 cm in diameter.

3. A padding material according to claim 1 wherein the thickness of the air bubbles is from 1 to 10 mm.

4. A padding material comprising a first moisture vapour permeable film layer and a second moisture vapour permeable film layer, a plurality of discrete air bubbles spaced between the first and second film layers and a plurality of discrete foam pips each of said foam pip being located in but not filling a respective air bubble.

5. A padding material comprising a water impermeable moisture vapour permeable film layer, an apertured moisture vapour permeable film layer and an intermediate adhesive layer and a plurality of discrete foam islands sandwiched between the apertured film layer and the adhesive layer.

6. A padding material according to claim 5 wherein the apertured film is a net.

7. A padding material according to claims 5 or 6 wherein the foam is hydrophobic.

8. A padding material according to claim 5 wherein the discrete foam islands are adapted to substantially interlock with adjacent foam islands when the padding is wrapped around a patient's limb.

9. A method of manufacturing a padding material comprising a first moisture vapour permeable film layer, a second moisture vapour permeable film layer, and a plurality of discrete foam pips spaced between said films, which method comprises:

(i) casting a moisture vapour permeable film onto a support layer;

(ii) coating the moisture vapour permeable film with an adhesive;

(iii) laying a plurality of discrete foam pips onto the adhesive layer;

(iv) laying a second film onto the adhesive layer; and (v) laminating the first film and the second film together.

10. A method of treatment of a fracture of a body portion which comprises applying a layer of undercast padding material according to claims 1, 4 or 5 followed by applying a hardenable casting material.

11. A kit comprising a padding material as claimed in claims 1, 4 or 5 and an orthopaedic casting tape.

12. A kit according to claim 11 wherein said casting material comprises a resin coated casting tape.

13. A kit according to claim 12 wherein said resin coated casting tape is water-hardenable.

* * * * *